(12) United States Patent
Sengupta et al.

(10) Patent No.: US 6,569,646 B2
(45) Date of Patent: May 27, 2003

(54) PROCESS FOR THE PRODUCTION OF AN ENZYME PREPARATION CONTAINING XYLANASE AND CARBOXYMETHYL CELLULASE FROM TERMITOMYCES CLYPEATUS HAVING ACCESSION NO 11CB-411

(75) Inventors: Subhabrata Sengupta, Calcutta (IN); Anil Kumar Ghosh, Calcutta (IN); Mohanlal Jana, Calcutta (IN); Amal Kumar Naskar, Calcutta (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/790,874

(22) Filed: Feb. 23, 2001

(65) Prior Publication Data

US 2002/0119532 A1 Aug. 29, 2002

(51) Int. Cl.$^7$ .......................... C12P 21/04; C12N 9/00; C12N 9/24; C12N 9/42; C12N 9/26
(52) U.S. Cl. ...................... 435/71.1; 435/183; 435/200; 435/201; 435/209
(58) Field of Search ................................ 435/183, 200, 435/209, 201, 71.1

(56) References Cited

PUBLICATIONS

Computer Biotechds 1995–08549 Abstract Sinha et al World J. Microtechnol (1995) 11, 3, 359–360.

Computer Biotechds 1984–0481 Abstract Sengupta et al "Biotech Bioeng" (1984) 26, 2, 188–190.

*Primary Examiner*—Herbert J. Lilling
(74) *Attorney, Agent, or Firm*—Rothwell, Figg, Ernst & Manbeck

(57) ABSTRACT

This invention relates to a process for the production of carboxymethyl cellulase and xylanase which comprises inoculating and growing *Termitomyces clypeatus* which has been deposited in the Indian Institute of Chemical Biology, Calcutta, one of the constituent laboratories of the applicant having accession no IICB-411, and at the Microbial Type Culture Collection (MTCC) at Chandigarh, India, an International Depository under the Budapest Treaty, under the accession no. MTCC 5091, in a sterilized medium containing assimilable carbon source, assimilable nitrogen source and micronutrients at a pH between 3 to 7, incubating the *Termitomyces clypeatus* at a temperature in the range of 25–30° C., separating the filtrate.

11 Claims, No Drawings

PROCESS FOR THE PRODUCTION OF AN ENZYME PREPARATION CONTAINING XYLANASE AND CARBOXYMETHYL CELLULASE FROM TERMITOMYCES CLYPEATUS HAVING ACCESSION NO IICB-411

FIELD OF THE INVENTION

This invention relates to a process for the production of an enzyme preparation containing xylanase and carboxymethyl cellulase, from *Termitomyces clypeatus* having accession no IICB-411 at the Indian Institute of Chemical Biology, Calcutta, India. The strain of *Termitomyces clypeatus* also has been deposited in the Microbial Type Culture Collection (MTCC) at Chandigarh, India, which has the status of an International Depository under the Budapest Treaty, under the accession no. MTCC 5091. The enzyme preparation is used in many industrial applications preferably for the treatment of textile, agro-products and plant biomass.

BACKGROUND AND PRIOR ART REFERENCES

Enzyme preparations containing xylanase and cellulase activities have many commercial uses as in liquefaction of fruit, vegetables, clarification of must juices, extraction of fruit juices, treatment of oil seed for better oil recovery, improving digestibility of cattle feed, smoothing of denim cloths, etc.

Cellulose and hemicellulose are the two major components of plant biomass. The basic molecular structure of cellulose is a linear polymer of glucose linked together by 1,4 β-glucosidic linkages. In mature cellulose containing 8,000 to 12,000 glucose units, the molecules are arranged in fibrils consisting of several parallel chains held together by hydrogen bonds. These fibrils are partly crystalline in nature. On the other hand, xylans are the major polysaccharide present in the hemicellulosic fraction of the plant biomass. These polysaccharides have a common backbone of 1,4 linked β-D-xylopyranoside units substituted with α-arabinofuranosyl, α-4-O-methyl glucuronosyl or acetyl group to different extents depending on the nature and maturity of the plant.

The microbial enzyme systems capable of hydrolysing cellulose and xylan are known as cellulolytic and xylanolytic enzymes respectively. Cellulolytic enzymes mainly consist of three types of enzyme;

1. Endoglucanase (1,4-β-D-glucan 4 glucanohydrolase, Enzyme Commission number 3.2.1.4) which acts on cellodextrin, substituted cellulose like carboxymethyl cellulose, swollen cellulose;
2. Cellobiohydrolase (1,4β-D-glucan cellobiohydrolase, Enzyme Commission number 3.2.1.91) which acts on native cellulose releasing cellobiose from non reducing ends of native cellulose, but does not attack substituted cellulose;
3. β-Glucosidase (β-D-glucoside glucohydrolase, Enzyme Commission number 3.2.2.21) hydrolyses cellobiose into glucose.

The endoglucanase activity, which is also known as carboxymethyl cellulase activity, is the major enzyme present in cellulolytic enzyme complex. Cellulase activity is generally measured in terms of carboxymethyl cellulase activity.

The enzyme endo 1,4β-xylanase (Enzyme Commission Number 3.2.1.8) which catalyses random hydrolysis of 1,4β-D-xylosidic backbone linkages of xylan is also the major enzyme on the xylanolytic enzyme complex. Endoxylanase activity is similarly taken as the measure of xylanolytic activity.

A large number of microorganisms including fungi, bacteria and actinomycetes produce cellulolytic enzyme which allow the them to grow on cellulose as the carbon source. But the extracellular enzyme activity liberated during growth of the cellulolytic microorganisms differs widely depending on the nature of the strain.

Among fungi, good extracellular enzyme producers are *Tricoderma reesei*, *Tricoderma koningii*, *Aspergillus terrus* and *Pellicularia filamentosa*. Bacteria like *Cellulomonas uda*, Ruminococcus sp, bacteriodes sp, *Clostridium thermocellum* are moderate producers of cellulolytic enzyme. Actinomycetes like Thermoactinomycete sp, Streptomyces sp, Thermopolyspora sp, were also reported to produce cellulolytic enzyme. Among all the strains fungi are good producers of cellulolytic enzyme, *Tricoderma reesei* being the best so far reported. Fungi produce both cellulolytic and xylanolytic enzymes together in media supporting either cellulase or xylanase production. Coproduction of cellulase and xylanase by bacteria or actinomycetes is rarely observed Among the microorganisms, yeast, bacteria and actinomycetes are also producers of xylanase. But fungi produce xylanase in much higher quantities than other microorganisms and bacteria and actiomycetes usually do not produce both xylanase and cellulase in a single fermentation. Of the fungal xylanases, production of the extracellular enzyme by *Aspergillus niger*, *Aspergillus fumigatus*, *Penicillium funiculosum*. Reference may be made respectively to Frederick, M. M., Kiang, C. H., Frederick, J. R. and Reilly, P. J. Biotechnol. Bioeng. 27, 525–532, 1985, Flannigan, B. and Sellars, P. N. Trans. Br. Mycol. Soc. 71,353–358, 1978), and Mishra, C., Seeta, R. and Rao, M. Enz. Microb. Technol. 7, 295–299, 1985. Among the basidiomycete, the Common Split Gill *Schizophyllum conmume* is a high producer of xylanase. Reference may be made to Postrochers, M., Jurasek, I. and Paice, M. G. Development Industrial Microbiology. 22, 675, 1981. Most of these organisms are highly cellulolytic in character and produce much higher amounts of cellulase than xylanase in the same fermentation. The mycelial culture of basidiomycete *Termitomyces clypeatus* having accession number IICB-411, developed and propagated by us and deposited at one of the constituent laboratories of the applicant is a good producer of both cellulolytic and xylanolytic enzymes in the same medium. However, the amount of xylanase and carboxymethyl cellulase produced by the strain varies depending on the composition of the medium. Reference may be made regarding the producer strain to S Sengupta, A K Ghosh, M L Jana and A K Naskar: A process for the production of xylanase solution without any detectable carboxymethyl cellulase activity (unpublished Indian patent application 353/DEL/94), S Sengupta, D. Sengupta, A K Naskar, M L Jana, A K Ghosh: An improved process for the preparation of bright juices from non-citus fruits (Indian Patent application no 365/DELI99), S Sengupta, A K Ghosh, A K Naskar, D Sengupta, M L Jana: A process for the preparation of an enzyme composition containing a mixture of pectinase and xylanase useful for clarification of non citrus fruit juice (Indian Patent application 686/DELI99), S Sengupta, D Sengupta, A K Naskar, M L Jana: A process for the preparation of a novel enzymatic formulation useful for improved leavening of bakery products (Indian Patent filed NF/403/99).

OBJECTS OF THE INVENTION

The main object of the present invention is to provide a process for the production of an enzyme preparation containing xylanase and carboxymethyl cellulase from *Termitomyces clypeatus* having accession no IICB-411 at the Indian Institute of Chemical Biology, Calcutta, India and accession no. MTCC 5091 at the Microbial Type Culture Collection (MTCC) at Chandigarh, India, an International Depository under the Budapest Treaty.

Another object of the invention is use of enzyme preparation for many industrial applications preferably, for the treatment of textile, agro-products and plant biomass.

SUMMARY OF THE INVENTION

Accordingly the present invention provides a process for the production of xylanase and carboxymethyl cellulase which comprises inoculating and growing *Termitomyces clypeatus,* which has been deposited in the Indian Institute of Chemical Biology, Calcutta, one of the constituent laboratories of the applicant having the accession No.IICB-411, and at the Microbial Type Culture Collection (MTCC) at Chandigarh, India, an International Depository under the Budapest Treaty, under the accession no. MTCC 5091, in a sterilized medium containing assimilable carbon source, assimilable nitrogen source and conventional micronutrients at a pH between 3–7 and incubating at a temperature in the range of 25–30° C., separating the filtrate by known methods.

DETAILED DESCRIPTION OF THE INVENTION

The present invention provides a process for the production of carboxymethyl cellulase and xylanase, said process comprising innoculating and growing the strain *Termitomyces clypeatus* which was isolated and propagated by the applicants and deposited in the Indian Institute of Chemical Biology, Calcutta, one of the constituent laboratories of the applicant having the accession No.IICB-411 and at the Microbial Type Culture Collection (MTCC) at Chandigarh, India, an International Depository under the Budapest Treaty, under the accession no. MTCC 5091.

In an embodiment of the present invention, the mycelial culture of *Termitomyces clypeatus* was characterized by different physical and biochemical properties.

Physical properties: The strain produces a silky white colony on solid medium, frequently producing aggression of mycelia in areas to form strands and knots of mycelia. The hyphae produced are tubular undifferentiated and hyphae of subcuits with short branches are also present. The average diameter of the hyphae is between 5 to 10 micrometer and all are septed. The strain under a microscope shows absence of any sporophoric structure or any basidiospore. A few clamp connections characteristic of mushroom culture also are visible within the hyphae. Hyphae with both single and double nucleus are present. The culture remains white over a long period of growth, say 10 to 15 days without any coloration due to any sporulation. Biochemical properties: The mycelial culture is a brown-rot type and has no phenol oxidase or laccase activity. It grows well in defined medium containing carbohydrate and mineral salts. The growth is not well supported by glucose but highly stimulated by glucose polysaccharides. The strain has optimum C/N ratio at 5 and 10 for optimum growth in synthetic medium. Trace elements like $Fe^{++}$, $Mn^{++}$, $Zn^{++}$, $Ca^{++}$ and $Mo^{++}$ have much influence on growth. The dry mycelia obtained in liquid medium at optimum growth phase has a composition of: protein 31.76%, carbohydrate 52.0%, fat 1.0%, fiber 10.5% and ash 2.7%. The strain in suitable medium gives positive tests for carboxymethyl cellulase, cellobiase, invertase, amylglucosidase, amylase, endo-xylanse, arabinofuranosidase, acety esterase and xylosidase activities but negative tests for laccase, phenol oxidase, chitinase and mannanase.

The strain was cultivated on a medium containing an assimilable carbon source, an assimilable nitrogen source, inorganic salts and organic nutrients. The assimilable carbon source includes carbohydrates such as glucose, xylose, mannose, arabinose, starch, dextrin, cellulose and xylan, agro-residue such as starch free wheat bran, corn cob powder saw-dust and amino acids such as aspartate, glutamate, serine and alanine. Assimilable nitrogen sources include ammonium salts like ammonium chloride, ammonium dihydrogen phosphate, ammonium nitrate and ammonium chloride, organic nitrogen such as soyapeptone and bactopeptone and organic nutrients such as malt extract, yeast extract, wheat bran and corn steep liquor. The fungus is maintained in agar-slant containing (w/v), malt extract 5%, potato extract 20%, glucose 5%, $KH_2PO_4$ 0.0874% pH 5.0. In the production of the enzyme composition, cultivation was carried out at a temperature between 25–30° C., preferably 29±1° C. under aerobic conditions in a shake flask in liquid medium on a rotary shaker at 200–300 strokes per minute. Among the assimilable carbon sources, xylan is the best carbon source with the concentration range from 0.5–2% (w/v), preferably 1% (w/v).

Among the assimilable nitrogen sources, bactopeptone, or ammonium sulphate or ammonium dihydrogen phosphate is preferred. Complex nutrients such as yeast extract (preferably from 0.5–1% w/v improves enzyme production by 2 fold) or, corn steep liquor (preferably 0.1–0.5 w/v) may be added. Presence of Tween-80 in an amount from 0.1 to 0.2% w/v improves enzyme production by 25–50%. Initial pH of the medium may be maintained from 3 to 7.0, preferably 3.5. Inoculum is developed in shake flask in a medium preferably containing (w/v) malt extract 5%, potato extract 20%, glucose 5%, $KH_2PO_4$ 0.0874%, 5.0 for 4 days. The mycelia obtained was suspended in sterile water and blended aseptically in a waring blender. Blended culture obtained from the volume of the inoculum medium was inoculated to ten volumes of fermentation medium (1:10 v/v). Optimum enzyme production in the culture filtrate took place between 4 to 5 days after inoculation. The enzyme produced in the culture filtrate was freed from fungal mycelia by filtration or centrifugation and used as the source of the enzyme.

In an embodiment of the present invention, the assimilable carbon source used is selected from carbohydrates selected from glucose, xylose, mannose, arabinose, starch, dextrin, cellulose, xylan, amino acids selected from the group comprising glutamate, aspartate, alanine and serine and agro residue selected from corncob powder, starch free wheat bran powder and any other sources.

In another embodiment of the present invention, the assimilable nitrogen source used is selected from ammonium salts selected from chloride, nitrate, dihydrogenphosphate and organic nitrogen selected from bacto-peptone, soya-peptone, malt extract, yeast extract wheat bran, corn steep liquor.

In still another embodiment of the present invention, the cellulose or agro residue employed ranges from 0.5 to 2.0%.

In yet another embodiment of the present invention, the optimum enzyme production by the strain takes place on 4 to 5 days of fermentation.

In yet another embodiment of the present invention, carboxymethyl cellulase and xylanase in the culture filtrate are optimally active between temperature range of 50° to 60° C.

In yet another embodiment of the present invention, carboxymethyl cellulase and xylanase activities of the culture filtrate are optimally active at a pH ranging from 5 to 6.

In yet another embodiment of the present invention, carboxymethylcellulase and xylanase are stable up to the temperature of 60° C.

Carboxymethylcellulase and xylanase activities present in the culture filtrate were assayed by Dinitro-salicylic acid method using caboxymethyl cellulose (soluble, sodium salt) and larch wood xylan as the substrates respectively. Reference may be made to Sumner, J. B. and Somers, G. F., 1949 in Laboratory experiments in biological chemistry, Academic Press, New York, pp.38-39

The invention is further illustrated with the following example, which should not be construed to limit the scope of the invention.

EXAMPLE 1

A culture medium consisting of (w/v): Cellulose powder 2, yeast extract 0.5, peptone 0.5, Tween-80, 0.2%, sucrose 2, $CaCl_2$, $4H_2O$, 0.0036%, $NaMoO_4$, 0.0032%, $FeSO_4$, $7H_2O$-0.027%, boric acid 0.057% and $NH_4H_2PO_4$-2.4%, pH 3.5 was prepared. One liter of medium was distributed as 50 mL of medium per 500 mL conical shaking flask and autoclaved at 15 pound per square inch pressure for 20 minutes. The medium was inoculated with aspetically blended mycelia of *Termitomyces clypeatus* having the accession No.IICB-41 previously grown in shake flasks for 5 days in a medium containing (w/v), malt extract 5%, potato extract 20%, glucose 5% and $KH_2PO_4$-0.0874% for 5 days at 29±1° C. with shaking. The culture broth was found to contain 200 units of xylanase and 190 units of carboxymethyl cellulase per mL as determined by dinitrosalicylic acid method. About 900 mL of culture filtrate was recovered by filtration of the culture filtrate under suction.

EXAMPLE 2

A culture medium containing (w/v)%: Starch free wheat bran powder 2, yeast extract 0.5, peptone 0.5, Tween-80-0.1 wheat bran 0.5, $CaCl_2$ $2H_2O$, 0.037, $MgSO_4$, $7H_2O$, 0.052, $MnCl_2$, $4H_2O$, 0.0036, $NaMoO_4$ 0.0032, boric acid 0.057%, $NH_4H_2PO_4$-2.4, pH 5.0 was prepared. Starch free wheat bran is prepared by removing contaminating starch by boiling with water, followed by digestion with amylase. One-liter of medium was distributed as 50 ml per 500 ml conical shaking flask and autoclaved at 15 pounds per square inch pressure for 20 minutes. The flask was inoculated asceptically with 10% (v/v) blended mycelia of *Termitomyces clypeatus* having the accession No. IICB-411 previously grown in shake flasks for 5 days in a medium containing (w/v)% malt extract 5, potato extract 20, glucose 5, and $KH_2PO_4$ 0.0874% for 4 days at 29±1° C. in a rotary shaker (200–250 rpm). Growth was contained for 4 days. The culture filtrate was filtered by suction. The units of xylanase and carboxymethyl cellulase activates as determined by the dinitrosalicylic acid method was found to be 300 units and 150 units per ml respectively. About 900 ml of the culture filtrate was recovered.

The Main Advantage of the Present Invention

1. The producer organism is an edible fungus and use of the enzyme preparation in the processing of any food preparation is not restricted.
2. The producer organism is an asporogenous mycelial culture and possibility for the development of fungal spore allergy is absent.
3. The optimum enzyme production by the strain takes place at 4 to 5 days of fermentation compared to other fungal fermentation, which takes a minimum of 7 days of fermentation.
4. Both carboxymethylcellulase and xylanase in the culture filtrate are optimally active between same temperature range of 50° to 60° C.
5. Both carboxymethylcellulase and xylanase activities of the culture filtrate are optimally active between same pH range of 5 to 6.
6. Both carboxymethylcellulase and xylanase are stable up to a temperature of 60° C.

What is claimed is:

1. A process for the production of carboxymethyl cellulase and xylanase which comprises inoculating and growing *Termitomyces clypeatus*, deposited at the Microbial Type Culture Collection (MTCC) at Chandigarh, India, under accession No. MTCC 5091, in a sterilized medium containing an assimilable carbon source, an assimilable nitrogen source and micronutrients at a pH between 3 to 7, incubating said *Termitomyces clypeatus* at a temperature in the range of 25–30° C. and separating the filtrate.

2. A process as claimed in claim 1, wherein the assimilable carbon source used is selected from the group consisting of carbohydrates, amino acids and agro residues.

3. A process as claimed in claim 1, wherein the carbohydrate is selected from the group consisting of glucose, xylose, mannose, arabinose, starch, dextrin, cellulose and xylan.

4. A process as claimed in claim 1, wherein the amino acid is selected from the group consisting of glutamate, aspartate, alanine, and serine.

5. A process as claimed in claim 1, wherein the agro residue is selected from the group consisting of corncob powder and starch free wheat bran powder.

6. A process as claimed in claim 1, wherein the assimilable nitrogen source used is selected from the group consisting of ammonium chloride, ammonium nitrate, ammonium dihydrogenphosphate, bacto-peptone, soya-peptone, malt extract, yeast extract, wheat bran, and corn steep liquor.

7. A process as claimed in claim 2, wherein the cellulose or agro residue is present at 0.5 to 2.0%.

8. A process as claimed in claim 1, wherein said separation of said filtrate takes place after 4 to 5 days of incubation.

9. A process as claimed in claim 1, wherein said culture filtrate contains carboxymethyl cellulase and xylanase activities which are optimally active at a temperature ranging from 50° to 60° C.

10. A process as claimed in claim 1, wherein said culture filtrate contains carboxymethyl cellulase and xylanase activities which are optimally active at a pH ranging from 5 to 6.

11. A process as claimed in claim 1, wherein said culture filtrate contains carboxymethyl cellulase and xylanase, activities which are stable up to the temperature of 60° C.

* * * * *